United States Patent [19]

Hudson

[11] 3,932,628

[45] Jan. 13, 1976

[54] EXTRACTS FROM ACTIVE TREE SAPS

[75] Inventor: Monie S. Hudson, San Jose, Costa Rica

[73] Assignee: The United States of America as represented by the Department of Health, Education and Welfare, Washington, D.C.

[22] Filed: June 14, 1973

[21] Appl. No.: 370,005

Related U.S. Application Data

[63] Continuation-in-part of Ser. No. 837,861, June 30, 1969, abandoned, and a continuation-in-part of Ser. No. 241,409, April 5, 1972.

[52] U.S. Cl. .............................................. 424/195
[51] Int. Cl.² ........................................ A61K 35/78
[58] Field of Search ..................................... 424/195

[56] References Cited
OTHER PUBLICATIONS

Hocking, A Dictionary of Terms in Pharmacognosy, Charles C. Thomas, Springfield, Illinois, pp. 185, 186–198 (1960).

Abbott et al., Cancer Research, Vol. 26, Part 2, Apr. 1960, No. 4, pp. 391–402 and 534.

*Primary Examiner*—Jerome D. Goldberg

[57] ABSTRACT

Extracts obtained from boiling displaced tree sap to dryness have significant anti-P388 mouse leukemia activity in mice.

14 Claims, No Drawings

EXTRACTS FROM ACTIVE TREE SAPS

This application is a continuation in part of Monie S. Hudson Ser. No. 837,861, filed June 30, 1969, for "Novel Composition and Method of Making the Same," now abandoned, and a continuation in part of Ser. No. 241,409, filed Apr. 5, 1972, for "Extracts from Active Tree Saps," also by Hudson, now pending.

The present invention relates to novel organic compositions derived from natural products, or specifically tree saps. The general subject of natural products and compounds is of current scientific interest (e.g., confer CEN, Feb. 28, 1972, page 58, re Maytansine and Dr. S. M. Kupchan of the University of Virginia). More particularly, this invention relates to dried extracts of specified tree saps which are further reconstituted in organic or aqueous media and have been utilized as antileukemia agents against mice afflicted with P388 mouse leukemia. It has been further found that only 5–10% of several hundred tree saps tested are active against P388 leukemia in mice.

Basically, then, this invention contemplates within its scope, novel compositions which are comprised of an effective dosage of a solid extract obtained from reducing liquid sap of plant life to a solid.

The sap of trees is particularly preferred for use in this invention for many reasons. For example, the extracts obtained from tree sap have been found to have very high anti-cancer characteristics. Furthermore, there enters in the practical consideration that only a very small amount of solid extract can be obtained from large volumes of liquid sap. Due to recent developments in the timber treating industry, wood or tree sap is now available at relatively low cost in large quantities. Still further is the practical consideration that trees are widely available while other plant life would probably have to be specially farmed over such a vast expanse of land to obtain sufficient sap so as to make their use impractical.

Furthermore, the investigation as here of the activity of dried tree saps appears to be a novel approach. For example, in a 1966 two-part publication emanating from the Cancer Chemotherapy National Service Center (C.C.N.S.C.-NIH) as follows:

Abbott et al., CR 26, Part 2, pages 391–398, 401, 402, and 534 (1966)

Abbott et al., CR 26, Part 2, pages 34, 41, 44, 45, and 151 (1966)

there are enumerated criteria for testing plants, bark, leaves, seeds, twigs, etc., particularly at page 401 above the similar codification at page 44. The investigation into the so-called "reconstituted" extracts of previously dried saps as in the present invention was a development and a scientific investigation subsequent to this 1966 protocol.

Examples of various types of trees from which sap may be extracted include:

TABLE I

| Kind of Tree | Botanical Name |
| --- | --- |
| Ailanthus | Ailanthus Altissma |
| Alder, smooth | Alnus Rugosa |
| Ash, Red | Fraxinus Pennsylvanica |
| Ash, Green | Fraxinus Pennsylvanica, var. Lanceolata |
| Ash, Prickly | Xanthoxylon Clava-Herculis |
| Aspen, Trembling | Populus Tremuloides |
| Basswood, white | Tilia Heterophylla |
| Beech, American | Fagus Grandifolia |
| Blue Beech | Carpinus Carolininiana |
| Birch, Black | Betula Lenta |
| Birch, River | Betula Nigra |
| Birch, White | Betula Papyrifera |
| Birch, Yellow | Betula Lutea |
| Box elder | Acer Negundo |
| Buckeye, yellow | Aesculus Octandra |
| Butternut | Juglans Cinerea |
| Catalpa, southern | Catalpa Bignonoides |
| Cedar, eastern red | Juniperus Virginiana |
| Cedar, northern white | Thuja Occidentalis |
| Cherry, black | Prunus Serotina |
| Cherry, pin | Prunus Pennsylvanica |
| Chestnut, American | Castanea Dentate |
| Chinaberry | Melia Azedarach |
| Cottonwood, eastern | Populus deltoides |
| Crabapple, flowering | Malus Baccata |
| Crabapple, southern | Malus Angustifolia |
| Crepe Myrtle | Lagerstroemia Indica |
| Cucumber tree | Magnolia Acuminata |
| Cypress, bald | Taxodium Distichum |
| Cypress, Arizona | Cupressus Arizonica |
| Dogwood | Cornus Florida |
| Elm, American | Ulmus Americana |
| Elm, Slippery | Ulmus Fulva |
| Elm, Winged | Ulmus Alata |
| Fir, fraser Balsam | Abies Fraseri |
| Gum, black | Nyssa Sylvatica |
| Gum, sweet | Liquidamber Stryaciflua |
| Gum, Swamp Tupelo | Nyssa Biflora |
| Gum, Water | Nyssa Aquatica |
| Hackberry | Celtis Occidentalis |
| Hawthorne | Crataegus, SSP |
| Hemlock, Eastern | Tsuga Caroliniana |
| Hemlock, Carolina | Tsuga Caroliniana |
| Hickory, Mockernut | Carya Tomentosa |
| Hemlock, Pignut | Carya Olabra |
| Hemlock, Shagbark | Carya Ovata |
| Hop Hornbeam | Ostrya Virginiana |
| Holly, American | Ilex Opaca |
| Holly, Mountain | Ilex Monticola |
| Laurel, Mountain | Kalmia Latifolia |
| Locust, Black | Robinia Pseudoacacia |
| Locust, Honey | Gleditsia Tricanthos |
| Magnolia, Fraser | Magnolia Fraseri |
| Magnolia, Southern | Magnolia Grandiflora |
| Magnolia, Sweetbay | Magnolia Virginiana |
| Maple, Mountain | Acer, Pennsylvanicum |
| Maple, Red | Acer, Rubra |
| Maple, Striped | Acer, Spicatum |
| Maple, Sugar | Acer, Saccharum |
| Mountain Ash | Sorbus Americana |
| Mulberry, Red | Morus Rubra |
| Myrtle, Wax | Myrica Cerifera |
| Myrtle, Saltwater | Myrica Heterophylla |
| Oak, Blackjack | Quercus Marilandica |
| Oak, Cherrybark | Quercus Falcata |
| Oak, Chestnut | Quercus Montana |
| Oak, Live | Quercus Virginiana |
| Oak, Eastern Red | Quercus Rubra |
| Oak, Scarlet | Quercus Coccinea |
| Oak, Water | Quercus Nigra |
| Oak, White | Quercus Alba |
| Oak, Willow | Quercus Phellos |
| Paulownia, Royal | Paulownia Tomentosa |
| Persia, Redbay | Persea Borbonia |
| Persimmon | Diospyros Virginiana |
| Pine, Jack | Pinus Banksiana |
| Pine, Loblolly | Pinus Paeda |
| Pine, Longleaf | Pinus Palustris |
| Pine, Pond | Pinus var. Serotina |
| Pine, Shortleaf | Pinus Echinata |
| Pine, Spruce | Pinus Glabra |
| Pine, Slash | Pinus Caribea |
| Pine, Tablemountain | Pinus Pungens |
| Pine, Virginia | Pinus Virginiana |
| Pine, White | Pinus Strobus |
| Plum, Chickasaw | Prunus Angustifolia |
| Poplar, Yellow | Liriodendron Tulopifera |
| Poplar, Carolina | Populus Canadensia var. Eugenia |
| Privet | Ligustrum Vulgare |
| Redbud | Cercis Canadensis |
| Rhododendron, Rosebay | Rhodendendron Maximum |
| Sassafras | Sassafras Varifolium |
| Serviceberry, Downy | Amelanchier Canadensis |
| Silverbell | Halesia Carolina, var. Monticola |
| Sourwood | Oxydendron Arboreum |
| Spruce, Black | Picea Mariana |
| Spruce, Red | Picea Rubens |
| Spruce, White | Picea Glauca |
| Sumac, Shining | Rhus Copallina |

TABLE I-continued

| Kind of Tree | Botanical Name |
| --- | --- |
| Sumac, Smooth | Rhus Glabra |
| Sumac, Staghorn | Rhus Typhina |
| Sycamore | Platanus Occidentalis |
| Ti-Ti | Cliftonia Monophylla |
| Walnut, Black | Juglans Nigra |
| Willow, Black | Salix Nigra |
| Willow, Coastalplain | Salix Longipes |
| Willow, Weeping | Salix Babalonica |
| Witchhazel | Hamamelis Virginiana |
| | |
| B 665330 | Prunus virginiana var. demissa |
| B 665339 | Leucothoe catesbaei |
| B 665426 | Genipa americana |
| B 665483 | Chrysophyllum brenesii |
| B 669806 | Sambucus racemosa var. arborescens |

In comparative activity this preferred group, together with B 669684 *Chiococca alba*, showed significant superiority in animal data screening.

As to this third group of tree saps, a slight change in protocol was made in the mice testing described in Example 6 post in that the current tests for determining T/C for lymphocytic leukemia P388 is described in Protocol 1.200 of Cancer Chemotherapy Reports, Part 3, Volume 3, No, 2, September, 1972, page 9, and as amended through Change No. 6 of May 1, 1973. In this mice testing protocol for this latter test, a natural product must have two different samples that produce a T/C ≥ 125% in multi-dose assays. The plant saps tested under the revised protocol are also listed and set out in Table II.

The sap from the plant life used in the invention may be obtained by any conventional method such as by crushing, bleeding, and the like. In those instances where tree sap is to be obtained, any one of a variety of methods for extracting the sap therefrom may be used.

Among the conventional techniques currently used for extracting sap from trees are the known bleeding (tapping) methods used by the maple syrup industry and a technique primarily concerned with preserving wood (logs) known as the Boucherie process after its founder.

Since for the input to the present invention tree sap in quantity is necessary, preferred methods of obtaining the sap usually proceed from felled timber where liquids under pressure force the sap from the tree. The basic "Boucherie" process, described in U.S. Pat. Nos. 111,784 Smith and 2,271,212 Tenger, was designed to replace the sap by a wood preservative but is best utilized for the present invention by using a non-contaminating liquid such as water or acetone.

Recently, improvements in the "Boucherie" process have appeared in patents and in a journal article as follows:

3,427,186 Hudson
3,443,881 Hudson
Hudson et al., FPJ 19, 25, No. 5, May 1969.

The improved techniques of 3,443,881 above, which use the end cap technique of "Boucherie" modified by removing at least one disc cut from the butt end intermediate in the process and the application of sequential liquid pressure treatment, are incorporated by reference in this application. This process is also known as the PRESCAP process and a preferred modification for the present invention is set out below.

As adapted for use in this invention, the PRESCAP technique preferably uses instead of a wood preservation as the first and/or second liquid, a harmless liquid of the same type used in the "Boucherie" process as adapted for use in this invention. Each liquid, such as water, acetone, or the like, may be the same or a different liquid for the two separate steps.

For example, one end (e.g., 6 to 10 inches) of a log from which sap is to be extracted, is debarked, placed and sealed in the above-described cap in a manner as described in the cited application. The first liquid, such as water, is then forced into the capped end of the log.

The time of treatment depends upon the liquid pressure used. For example, a liquid pressure of 200 psi applied for about 2½ minutes is very effective.

In those instances where disc removal is desirable, treatment with the first liquid is then stopped and the log is removed from the cap whereinafter a thin disc of wood (e.g., between ⅛ - 1 inch in thickness) is removed from the treated end of the log. The log is again resealed in the cap and a second treating liquid, e.g., water, acetone, or the like, is forced through the log to displace sap from the opposite end thereof. The sap is then collected and treated as hereinafter described.

In a particularly preferred technique of collecting sap, optimum effects may be achieved by first extracting sap with acetone and then entirely re-extract the same log using water. In this respect, the entire procedure as described above is run using water as first and second liquid. In so doing, it is found that the acetone treatment will substantially increase the water extractive yield.

It is understood, of course, that extraction of sap is continued until the liquid issuing from the collecting end of the log no longer contains a practical amount of sap. Such a point is easily determined by the skilled artisan using conventional techniques.

An additional preferred process is set out in U.S. Pat. No. 3,427,186 Hudson, supra, which process is also

TABLE II

| | | Screening Results of Plant Saps Active in Leukemia P388 | | | | | |
| --- | --- | --- | --- | --- | --- | --- | --- |
| NSC No. | Name | Locality | Highest T/C Code 15[1], T/C dose | | B001/2 dose | | B002/3 dose |
| 330 | Prunus virginiana var. demissa | Calif. | 131 | 25 | 161 | 16[2] | 145 | 120[3] |
| 339 | Leucothoe catesbaei | N.C. | 150 | 50[4] | 150 | 35 | 140 | 50[5] |
| 426 | Genipa americana | Costa Rica | 150 | 200[1] | 175 | 200[1] | 160 | 100 |
| 483 | Chrysophyllum brenesii | Costa Rica | 144° | 50 | 147 | 25 | 150 | 25 |
| 806 | Sambucus racemosa var. arborescens | Wash. | 133; 137 | 75 | 150 | 165[5] | 150 | 400[1] |

[1]Active also at 100.
[2]Active also at 11.
[3]Active also at 50.
[4]Active also at 12.5
[5]Active also at 35 known as the SLURRY-SEAL process where a slurry of solid particles is utilized to blanket and form a seal over a length of wood for subsequent impregnation or liquid pressure treatment. The specific techniques utilized as taught in 3,427,186 are also incorporated by reference here.

After obtaining the raw sap product by use of the above-described techniques, the extract of this invention may be obtained therefrom. Most conveniently, the extract is obtained by boiling the collected sap to dryness using known apparatus such as large pyroceram boiling kettles or the like. In this respect, it has been found that for optimum results the sap should be collected and the crude extract obtained therefrom as soon after the tree is cut as possible. This is because biological processes set in rapidly after a tree is cut, to change chemistry of the wood and the compounds therein. Generally speaking, the sap should be collected and the extract obtained within about 30, and preferably 15, days from the time the trees are initially cut. Such a time period, of course, is only general, since optimum results vary as the type of tree, time of the year, etc., is varied.

Large quantities of raw sap are usually required to obtain a usable amount of the extract of this invention. The actual amount of sap needed will, of course, vary with the type of wood and the time of the year. As alluded to hereinbefore, optimum yields are usually obtained from many trees just prior to their production of new growth (e.g., just prior to budding in the spring or late winter). In Northern America, such times usually occur about January through March, and even December has been found to be an excellent month.

Exemplary of the yields to be expected, in late March, 4 gallons of sap collected from each of Black gum, Sweet gum, Sourwood, Dogwood, and Black cherry trees yielded a dry solid extract as contemplated by this invention of from about 30 to 50 grams. The same amount of sap from these species collected in late May yielded only 1 or 2 grams of extract. Such low yields continued until about one month after leaf fall in October and November whereinafter, starting with December the yields returned to the 30 to 50 gram yield level.

For evergreens, it is noted, this marked seasonal difference does not appear, since yields remain substantially constant all year long. Examples of such evergreens include pine, cedar, and firs. Other species which exhibit constant yields similar to evergreens include southern magnolia, holly, persea, and the like.

As can be seen from the above, even though some yields are referred to as "high," they are, indeed, relatively low with respect to many commercial chemical processes. It is, therefore, apparent why the use of fast sap collecting techniques are most desirable.

As alluded to hereinabove, the solid extract, once obtained, may be used in its "raw form" or as a reconstituted extract prepared from the dried or "raw" sap. For this reason, this invention contemplates within its scope a novel compound comprised of an effective amount of plant life sap extract as described.

EXAMPLE 1

Each of the preferred extracts prepared and noted in Table II were recovered from trees by the Prescap Process extracts were tested for their anticancer effect using the Standard Leukemia Test as reported in Cancer Chemotherapy Reports, No. 25, Dept. of Health, Education, and Welfare, December 1962, pp. 1–66. The disclosure of this report is incorporated herein by reference. Basically, the procedure used is as follows:

Healthy mice, about 3 months old, and weighing about 20 grams (0.7 ounces) were injected with a virulent strain of mouse leukemia designated P-388. For each test of an extract, 12 mice were used. Six of the mice were left untreated after contracting leukemia (i.e., after being injected with P388), while the remaining six mice were injected intraperitoneally once daily for 10 days using the indicated dosage of extract dissolved in water.

Survival time of each of the 12 mice was then recorded. The survival time of the untreated or control mice was designated as C, while the survival time of treated mice was designated as T.

The protocol for determining activity is as follows. The extract is given a preliminary approval of Code 11 or Code 13, where a $T_1/C_1$ value of 125 or better indicating 125% longevity of the treated animal over the control. If satisfactory activity is obtained directly, a Code 11 rating is achieved. If, however, the dosage must be modified for toxicity reasons to obtain the necessary activity, then a Code 13 rating is given the extract or compound. Where a second test indicates such a $T_2/C_2$ value where the product $T_1/C_1 \times T_2/C_2 -$ 156, the extract is given a Code 15 rating having passed the biological animal (mouse) screen and in the protocol or hierarchy of the C.C.N.S.C. is now a candidate for confirmatory tests. In the above formula, the values for T and C indicate mean treatment/control time for the mouse.

The results below indicate that each of the tree sap extracts possessed activity at least at the level of Code 15 as read from Screening Data Summary, C.C.N.S.C. (No. 14 of December 1970), which is incorporated by reference to this invention.

Once a Code 15 rating is achieved, additional toxicity testings varying the dosage on the same sample (BOO1) and on a separate sample (BOO2) are performed to confirm activity.

Of the more recently obtained varieties processed and tested by standard biological tests, the following exhibited activity of comparatively lower dosage ranging in T/C dosage from 75–5 mg/kg per diem and, the BOO1 dosage was depressed with activity at 3.3 mg/kg per diem:

B 669684 Chiococca alba

The following table (Table III) illustrates the results of this testing which was conducted by the Cancer Chemotherapy National Service Center for Natural Products, National Cancer Institute, of Bethesda, Maryland.

TABLE III

Screening Results of Plant Saps Active in Leukemia P388

| NSC No. | Name | Locality | Highest T/C Code 15.T/C | dose | B001/2 | dose | B002/3 | dose |
|---|---|---|---|---|---|---|---|---|
| B 669684 | Chiococca alba | Fla. | 140;127 | 5 | 150 | 7.5[1] | 130 | 7.5[2] |

[1]Active also at 3.3
[2]Active also at 5

The embodiments of this invention in which an exclusive property or privilege is claimed are defined as follows:

1. A method of treating P388 leukemia in mice which consists in injecting into said mice an effective amount for treating P388 leukemia of a tree sap which has been produced by extracting with water and subsequently dried and which tree is selected from the group consisting of:
   Prunus virginiana var. demissa
   Leucothoe catesbaei
   Genipa americana
   Chrysophyllum brenesii
   Sambucus racemosa var. arborescens and
   Chiococca alba 2. The method according to claim 1 wherein the tree sap is *Prunus virginiana* var. *demissa*.

3. The method according to claim 1 wherein the tree sap is *Leucothoe catesbaei*.

4. The method according to claim 1 wherein the tree sap is *Genipa americana*.

5. The method according to claim 1 wherein the tree sap is *Chrysophyllum brenesii*.

6. The method according to claim 1 wherein the tree sap is *Sambucus racemosa* var. *arborescens*.

7. The method according to claim 1 wherein the tree sap is *Chiococca alba*.

8. A composition for the treatment of P388 mouse leukemia which comprises a pharmaceutically acceptable carrier and an effective amount to treat P388 mouse leukemia of a tree sap which has been produced by extracting with water under 200 psi and subsequent drying and wherein the tree is selected from the group consisting of *Prunus virginiana* var. *demissa*, *Leucothoe catesbaei*, *Genipa americana*, *Chrysophyllum brenesii*, *Sambucus racemosa* var. *arborescens*, and *Chiococca alba*.

9. The tree sap according to claim 8 wherein the sap is *Prunus virginiana* var. *demissa*.

10. The tree sap according to claim 8 wherein the sap is *Leucothoe catesbaei*.

11. The tree sap according to claim 8 wherein the sap is *Genipa americana*.

12. The tree sap according to claim 8 wherein the sap is *Chrysophyllum brenesii*.

13. The tree sap according to claim 8 wherein the sap is *Sambucus racemosa* var. *arborescens*.

14. The tree sap according to claim 8 wherein the sap is *Chiococca alba*.

* * * * *